United States Patent
Hardman et al.

(10) Patent No.: US 7,286,633 B1
(45) Date of Patent: Oct. 23, 2007

(54) FUEL ANALYSIS SYSTEM

(75) Inventors: Peter John Hardman, Woburn, MA (US); Bradley Hubbard-Nelson, Concord, MA (US)

(73) Assignee: Innov-X Systems, Inc., Woburn, MA (US)

( * ) Notice: Subject to any disclaimer, the term of this patent is extended or adjusted under 35 U.S.C. 154(b) by 0 days.

(21) Appl. No.: 11/585,367

(22) Filed: Oct. 24, 2006

(51) Int. Cl.
*G01N 23/223* (2006.01)

(52) U.S. Cl. .......................................... 378/47; 378/45

(58) Field of Classification Search ............. 378/44–50

See application file for complete search history.

(56) References Cited

U.S. PATENT DOCUMENTS

| 5,220,591 | A | * | 6/1993 | Ohsugi et al. ................. 378/45 |
| 5,598,451 | A | * | 1/1997 | Ohno et al. .................... 378/44 |
| 6,859,517 | B2 | | 2/2005 | Wilson et al. |

* cited by examiner

*Primary Examiner*—Hoon Song
(74) *Attorney, Agent, or Firm*—Iandiorio & Teska (57) ABSTRACT

A fuel analysis system and method wherein an x-ray source emits x-rays at an energy level below but proximate the absorption edge of sulfur. A monochromator is in the optical path between the source and a fuel sample for directing x-rays at a single energy level at the fuel sample to limit excitation of any sulfur in the fuel sample. A detector is responsive to x-rays emitted by the sample and an analyzer is responsive to the detector and configured to determine the amount of silicon and aluminum in the sample.

8 Claims, 7 Drawing Sheets

FUEL ANALYSIS SYSTEM

FIELD OF THE INVENTION

This subject invention relates to an x-ray fluorescence (XRF) system and, more particularly, to such a system well suited to measure the concentrations of catalyst fines in fuel oil.

BACKGROUND OF THE INVENTION

Crude oil is processed by a variety of means to produce the valuable light fractions such as gasoline, kerosene, and the like. Since these products are valuable commodities, it makes economic sense to try and convert as much of the oil as possible to these components. As much as 75% of a barrel of oil can be utilized in this way by a combination of distillation and catalytic cracking. In catalytic cracking, the heavy oil components which were left over from distillation are broken into smaller molecular weight components with the aid of a cracking catalyst. The catalysts are porous aluminum-silicate structures. At the end of the cracking process the material which was not broken down remains in the product. The sludge oil contains significant amounts of catalysts, called "fines" or "catfines" typically as very small particles (0.1 to 8 um) in size. The sludge oil is mixed with other feedstock to produce the heavy fuel oils used for large marine diesel engines. The presence of high (>80 ppm) levels of aluminum and silicon and other catalyst fines in the fuel can cause problems when the fuel is injected into the engine. The catalyst fines are very hard materials which can cause rapid wear on the engine components such as the cylinder, pistons and valves. For this reason, one standard dictates that all fuel must be prepared with a total combined Al+Si concentration of <80 ppm.

Fuel oil analysis often involves several specialized pieces of equipment operated by scientists in a laboratory. The current method used for measuring low concentrations of catalyst fines is an ISO method, ISO 10478: 1994. This standard method states that the amount of aluminum and silicon should be measured by using Inductively Coupled Plasma (ICP) spectroscopy analysis. ICP is a sensitive technique that is able to measure most elements down to the 1-10 ppb level in the sample introduced into the spectrometer. However, the ICP technique requires that the sample be in liquid form so that it can be sprayed into the plasma. This means that for solid samples or viscous liquids, some form of dissolving and dilution is required. Then, the detection limits in the original sample are 10-100 times higher, depending on the amount of dilution that has occurred. The major drawbacks of ICP for testing in the field (e.g., on-ship or dockside) are that such systems are relatively expensive instruments that use expensive consumables such as liquid Argon, and are not portable. In addition this method is time consuming and requires several analytical steps that require a skilled technician to carry out the procedure.

X-ray fluorescence (XRF) is a non-destructive technique used to analyze samples with a minimum of preparation. To make a compact XRF spectrometer, however, requires the use of an energy dispersive detector. This means that the detector collects and measures all energies simultaneously. The detector electronics separates out the different x-rays. The alternative is a "wavelength dispersive" system which separates the x-rays into different energies by using a crystal. The x-rays of each single energy are then counted sequentially.

The elements in the catalyst fines (Al and Si) are amongst the lightest elements that can routinely be measured at low levels with XRF. In a typical bench top XRF system, the detection limits for these elements are typically 500-1000 ppm, which is 100 times larger than is required for accurate quantification of Al and Si in fuel. Hence, there are several technological problems which must be overcome.

The fluorescent x-rays from Al and Si have relatively low energies of 1.486 keV and 1.740 keV respectively. These x-rays travel a relatively short distance through solids or air before being absorbed.

The yield of x-rays from elements is proportional to the atomic number Z. This means that for every x-ray absorbed by an atom, the chance of producing a fluorescent x-ray is low for Al and Si. The highest probability of producing a fluorescent x-ray occurs when the exciting x-ray is at just a slightly higher in energy than the energy to be emitted. This means that to best excite Al and Si with the same x-rays, an ideal energy of approximately 2 keV is needed. But, most x-ray tubes have a very low intensity output at such a low energy due to a relatively thick Be window (75 um) which cuts out much of the intensity below 2 keV and also because the standard anode materials used have no lines in this region of the spectrum.

In heavy fuels there is a further complication, in that the fuel contains greater than 0.5% sulfur. In some cases the sulfur content can be as high as 5-6%. In an energy dispersive XRF system, the amount of data that can be collected per second is limited by the x-ray detector. The presence of high levels of sulfur affects both the amount of Al and Si x-rays which can be collected and also changes the shape of the spectrum in the region where Al and Si are observed.

Moreover, XRF techniques for analyzing fuel oils have not yet been employed in the field because the laboratory equipment used for the analysis is not engineered for use outside of a laboratory.

SUMMARY OF THE INVENTION

It is therefore an object of this invention to provide a new fuel oil analysis system.

It is a further object of this invention to provide such a system which can be used in the field by technicians and other personnel.

It is a further object of this invention to provide such an analysis system which limits the excitation of sulfur in the fuel oil sample and reduces the background signal of the exciting radiation.

It is a further object of this invention to provide such a system which is ergonomic and robust in design.

The subject invention results from the realization that an ergonomic and robust analysis system able to better detect and quantify catalyst fines in a fuel oil sample is effected by the use of an x-ray source which emits x-rays at an energy level below but proximate the absorption edge of sulfur in combination with a monochromator which limits the amount of scattered tube radiation and prevents the excitation of any sulfur in the fuel sample.

The subject invention, however, in other embodiments, need not achieve all these objectives and the claims hereof should not be limited to structures or methods capable of achieving these objectives.

The subject invention, in one embodiment, features a fuel analysis system comprising an x-ray source (e.g., a molybdenum anode x-ray tube) which emits x-rays at an energy level below but proximate the absorption edge of sulfur. A monochromator is located in the optical path between the source and a fuel sample for directing x-rays at a single energy level at the fuel sample to limit excitation of any sulfur in the fuel sample. A detector is responsive to x-rays emitted by the sample and an analyzer is responsive to the detector and is configured to detect and typically determine the amount of at least one catalyst fine in the sample.

The preferred monochromator includes doubly curved crystals. Typical catalyst fines include silicon and aluminum and the system is also able to detect low levels of sodium, magnesium, and phosphorous.

A fuel analysis method includes directing x-rays at a single energy level below but proximate the absorption edge of sulfur at a fuel sample to limit excitation of any sulfur in the fuel sample, detecting x-rays emitted by the sample, and determining amount of at least one element present in catalyst fines contaminating in the sample.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 1:
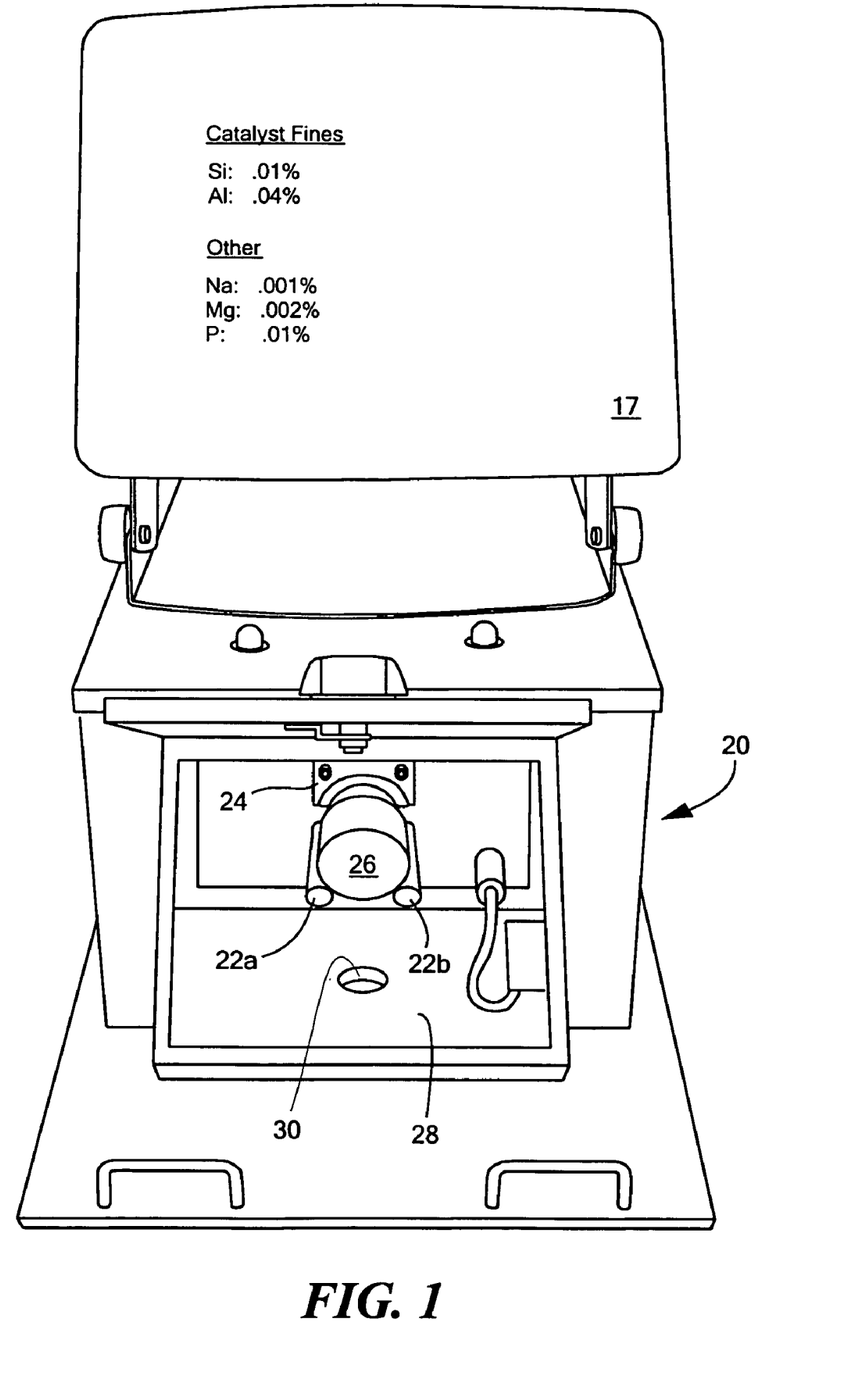
FIG. 1 is a schematic three-dimensional view of an example of one preferred fuel analysis system in accordance with the subject invention.

FIG. 1 is a depiction of one example of an XRF system in accordance with this invention engineered to detect and measure the concentrations of catalyst fines in a fuel oil sample. In one preferred embodiment, a sample holder includes posts 22a and 22b and sample adapter 24 which position sample holder 26 within unit 20. The fuel oil analysis system of the subject invention, however, need not be engineered the same as the XRF system shown in FIG. 1.

Figure 2:
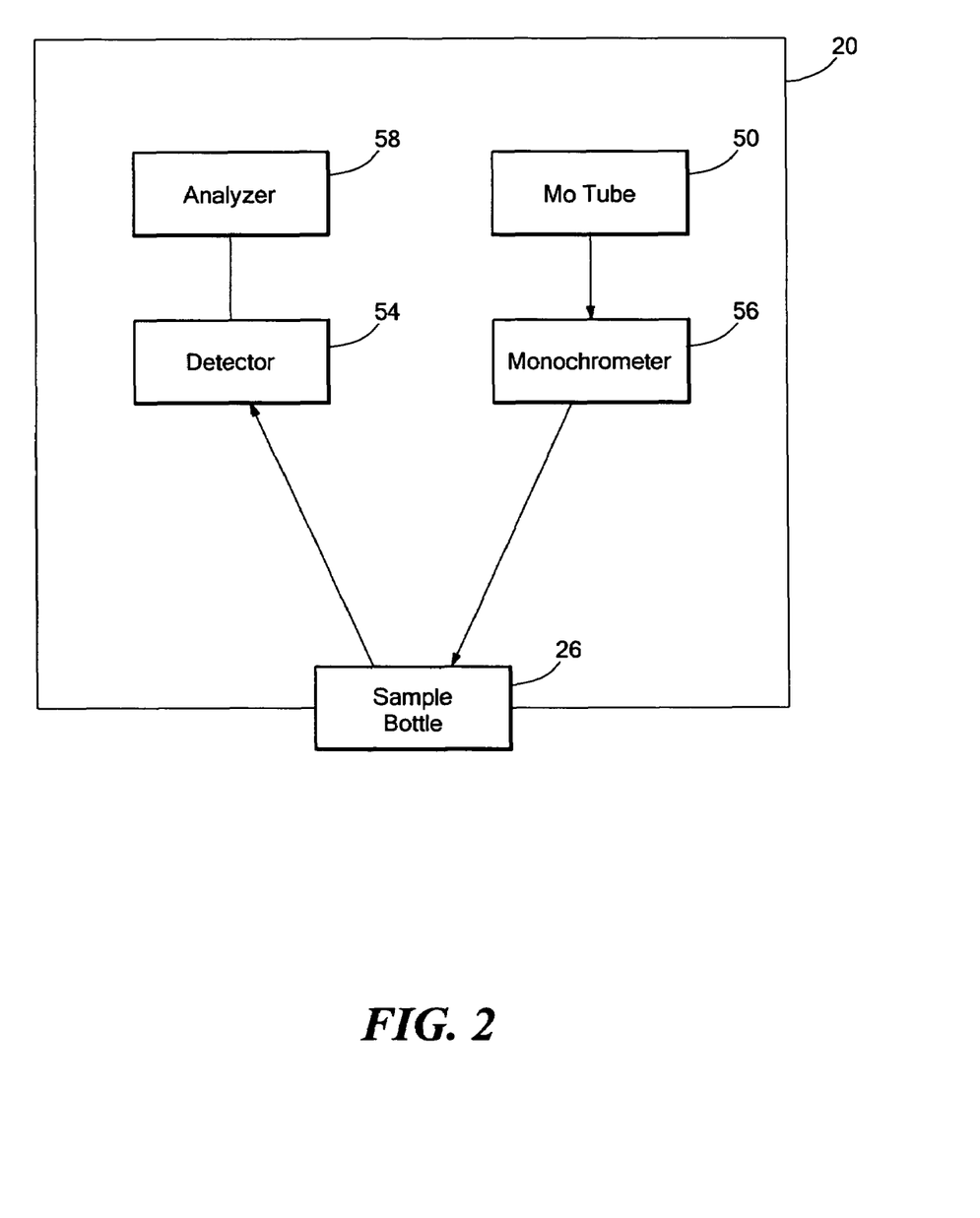
FIG. 2 is a schematic block diagram showing the primary components associated with the analysis system shown in FIG. 1.

FIG. 2 shows the primary components associated with an exemplary analyzer unit 20. X-ray source 50 emits x-rays which are directed to a sample 26. X-rays emitted by the sample in the bottle are directed to detector 54. The preferred x-ray source 50 is a molybdenum anode x-ray tube which emits x-rays at an energy level below but proximate the absorption edge of sulfur at about 2.293 keV. A monochromatizing component 56 is located in the optical path between x-ray source 50 and sample 26. The monochromatizing component could comprise doubly curved crystals (e.g., X-ray Optical Systems, Inc., East Greenbush, N.Y.), HOPG Optics, (e.g., Optigraph GmbH, Berlin, Germany), multilayer optics (Incoatec GmbH, Geesrhacht, Germany), or other appropriate technology. Monochromator 56 directs x-rays at a single energy level at the fuel oil sample 26 to limit excitation of any sulfur in the sample. Other devices, such as a grating, however, may be used to provide a monochromatic x-ray beam directed at the sample. Analyzer 58 is responsive to detector 54 and is configured to determine the amount of catalyst fines in the sample, typically silicon and aluminum but also sodium, magnesium, and phosphorus. The signal output by detector 54 is analyzed by analyzer 58 where the energy levels of the detected x-ray photons are divided into several energy subranges by counts of the number of x-ray photons detected to arrive at an x-ray spectrum of the sample.

It is highly advantageous that system 20 not be sensitive to the amount of sulfur (S) in the sample. In this invention, an excitation energy is chosen which efficiently excites aluminum (Al) and silicon (Si), but does not excite sulfur (S).

The most efficient energy to excite Si and Al is at around 1.9 keV. But, from an analysis point of view, 1.9 keV is too close to the Si peak at 1.740 keV to be easily separated using an energy dispersive detector. To produce energies in this region, a Zirconium (Zr) L-alpha=2.042 keV or Niobium (Nb) L-alpha=2.166 keV source would be required. For an energy dispersive system, these lines are not effective as they lie too close to the elements of interest and would make seeing small amounts of Si difficult. To make this system effective it turns out that the best x-ray energy to use is around 2.2-2.3 keV which is where the Mo L-alpha line is situated at 2.293 keV. The next practical x-ray tube to use after Molybdenum is Rhodium (Rh) which has its L-alpha line at 2.696 keV. This line is above the excitation threshold for sulfur which means that a Rh tube will very efficiently excite sulfur and thus is not a preferred anode material.

Figure 3:
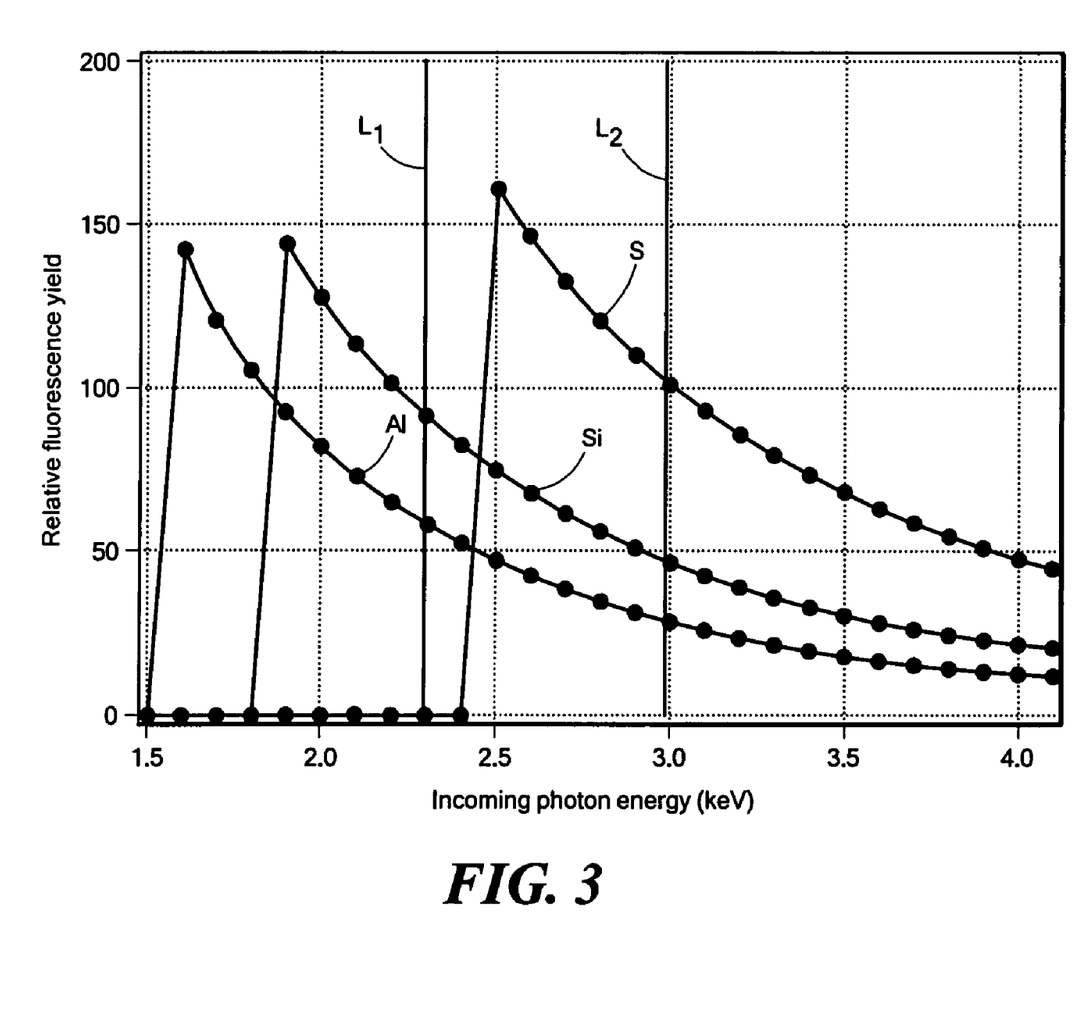
FIG. 3 is a graph depicting the relative fluorescence yield at various energy levels for aluminum, silicon, and sulfur.

FIG. 3 shows the relative number of x-rays produced from an element as a function of excitation energy. If the Mo-L line $L_1$ is used, Al and Si are excited at approximately 50-75% efficiency, but sulfur is not excited at all. If an Ag tube source were used ($L_2$), the sulfur efficiency would be twice higher than Al and Si. Since the sulfur is at levels 1000 times higher than the Al and Si, only the sulfur would be detected; not the catalyst fines. A system which uses Mo-L alpha is actually able to efficiently excite Na, Mg, Al, Si and P. So, additional elements besides Al and Si can be detected as well.

Figure 4:
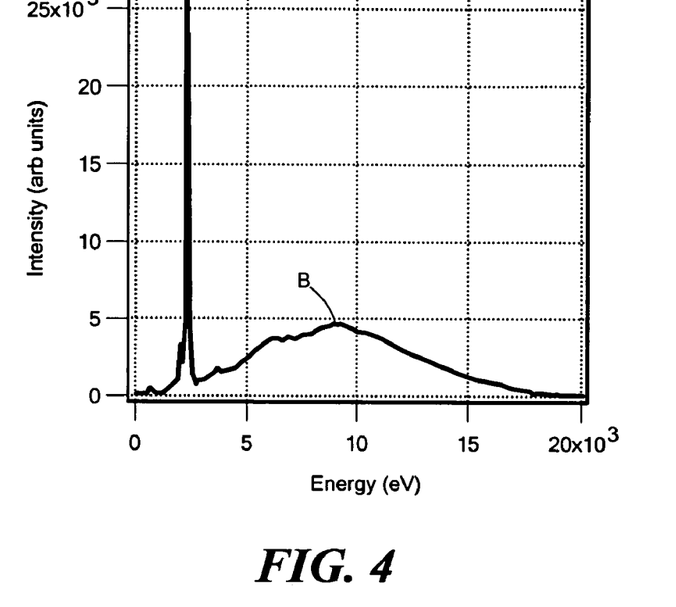
FIG. 4 is a graph showing intensity versus energy level for a molybdenum anode x-ray tube without a monochromator.
Figure 5:
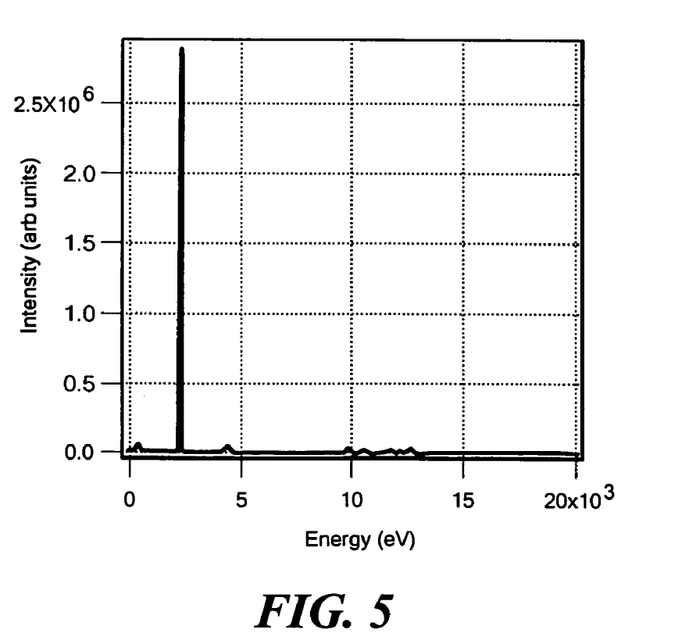
FIG. 5 is a graph showing intensity versus energy level when a monochromator is located in the optical path between the molybdenum anode x-ray tube and the sample in accordance with this invention.

However, if a Mo anode x-ray tube is used to measure the sample without any filtering or monochromatization, then the whole spectrum would have a sloping background which the peaks of interest sit on. And, as shown in FIG. 4, the excitation spectrum extends up to the maximum voltage of the x-ray tube. This sloping background B can change with the S concentration in the sample. When the tube spectrum is passed through the monochromator, however, as shown in FIG. 5, only one energy is allowed to pass and the excitation spectrum becomes mono-energetic. This means that the peaks of interest sit on a flat background and are better defined. This also improves the efficiency of the measurement process because all the higher energy x-rays from the tube are not detected and counted, because they were removed by the monochromator.

Figure 6:
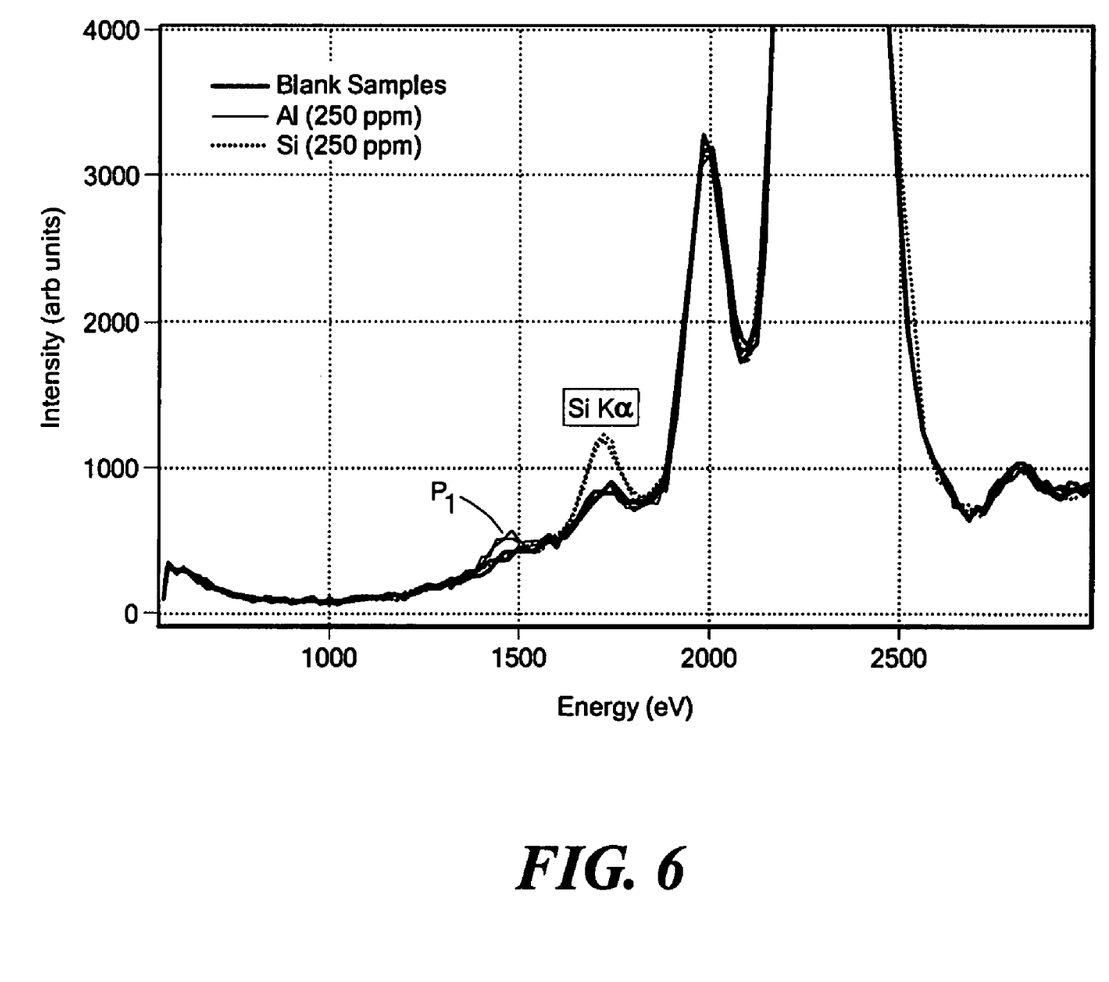
FIG. 6 is a graph depicting detected intensity versus energy level for three samples when a monochromator is not used.
Figure 7:
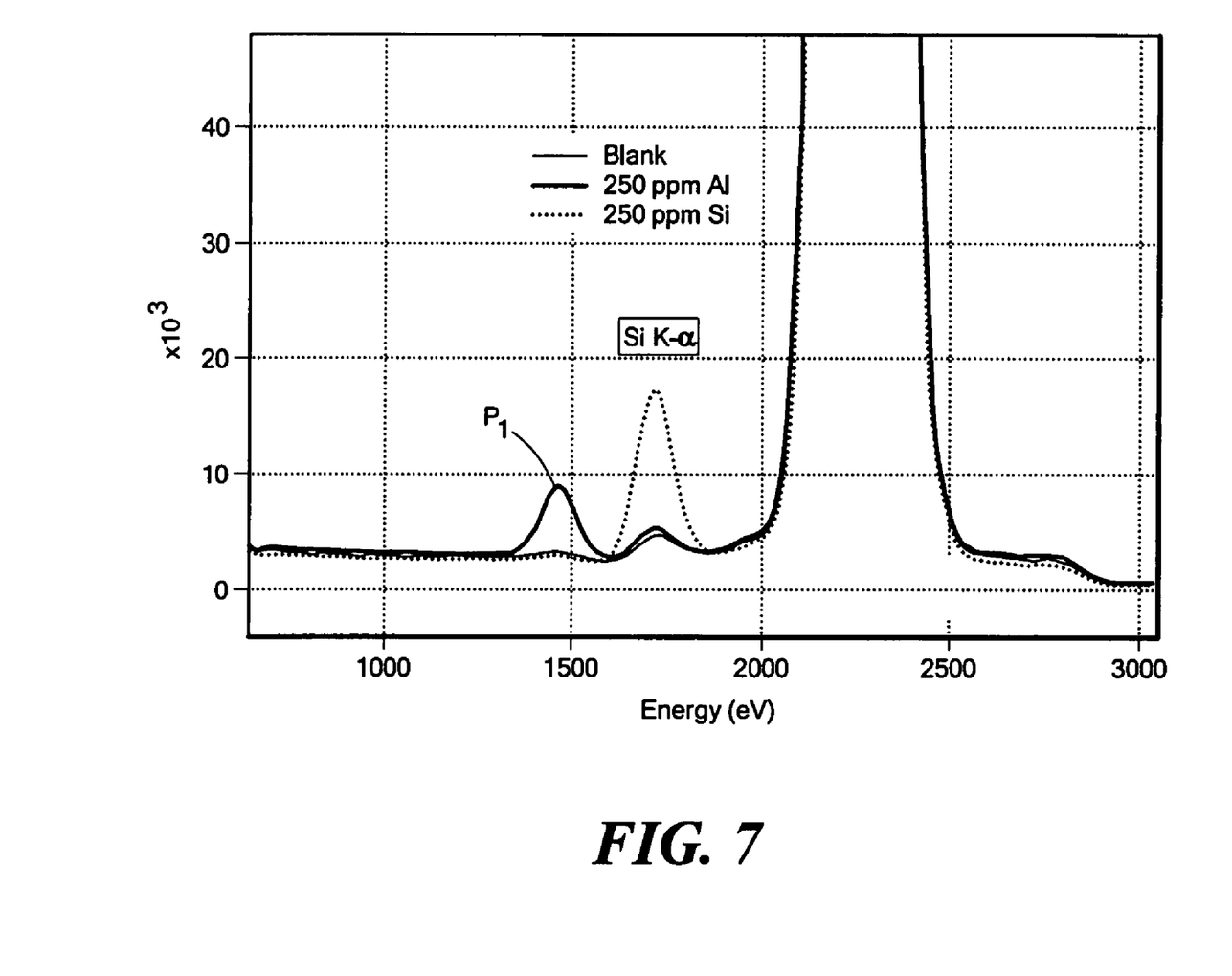
FIG. 7 is a graph depicting detected intensity versus energy level for three samples when a monochromator is used in accordance with the subject invention.

FIG. 6 shows the results without monochromator 56, FIG. 2 and FIG. 7 shows the results with monochromator 56. Note the ability to ascertain Al peak $P_1$ in FIG. 7 but not in FIG. 6.

Figure 8:
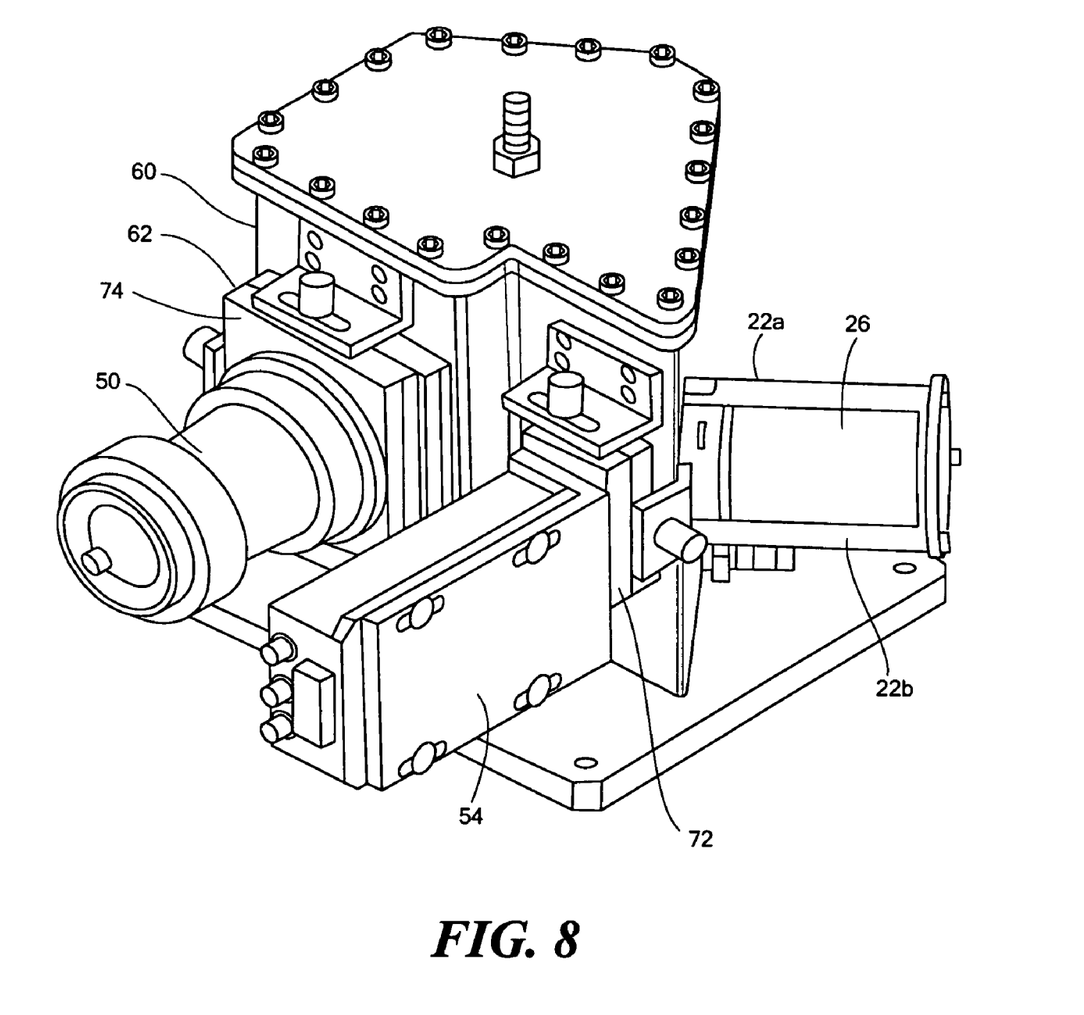
FIG. 8 is a schematic three-dimensional view showing the primary components associated with one preferred version of a fuel oil analysis system in accordance with the subject invention.

As shown in FIG. 8, one preferred optics housing 60 includes therein monochromator 56 in one embodiment. Attached to optics housing 60 is molybdenum anode x-ray tube source 50, detector 54, and sample holder posts 22a and 22b. The other primary components include cover 64, curved crystal mounting bracket 66, bottom plate 68, detector bracket 70, and slide plate assemblies 72 and 74. Display 17, FIG. 1 and analyzer 58, FIG. 2 are not shown in FIG. 8.

Molybdenum anode x-ray tube 50, FIG. 2 preferably emits characteristic L-alpha x-rays at an energy level, FIG. 3, of 2.293 keV below but proximate the absorption edge of sulfur at about 2.472 keV. Monochromator 56, FIG. 2 directs x-rays at the sample at a single energy level as shown in FIG. 5 to exclude excitation of any sulfur atoms in the fuel sample which are in background region B in FIG. 4 and to reduce the background from the tube radiation.

As a result, the percentage or other quantifying measurement of the catalyst fines in a fuel sample can be detected and displayed on display 17, FIG. 1. A technician, in the field, is able to place a fuel sample into XRF analysis system 20, and be provided with a record of, inter alia, the amount of catalyst fines in a fuel sample. The preferred system is ergonomic in design and robust for use in the field. In any embodiment, the analysis system of the subject invention is able to better detect and quantify catalyst fines in a fuel oil or other sample by the use of a molybdenum anode or another x-ray source which emits x-rays at an energy level below but proximate the absorption edge of sulfur in combination with a monochromator which limits excitation of any sulfur in the fuel sample. Because the low energy x-rays are easily absorbed, even by air, it is sometimes necessary to reduce the distances in the spectrometer as much as possible, and to evacuate enclosure 20, FIG. 1 or flush the x-ray path with Helium, for example, to achieve good sensitivity.

For the analysis of catalyst fines in fuels in the field (on board a ship or in port), the use of a Helium atmosphere may not always be appropriate. This is due to the problems of obtaining consumables, and also the chance of asphyxiation in an enclosed area on a vessel. One option is to surround the sample with a vacuum instead of helium to measure catalyst fines.

In general, placing liquids in a vacuum is not a good idea. However, an additional property of fuel oils can be used to an advantage. Because fuel oils did not distill or crack, they have a very low vapor pressure, which means that they are actually quite stable in a vacuum at room temperature. This means that the sample can be placed directly into a vacuum and a "sample window" is not needed between the source, the sample, and the detector.

Also, only a small amount of sample is needed to successfully make a measurement of the catalyst fines concentration, because even in a large sample (cm in depth) only the top 100 um contributes to the final result. It is therefore possible to prepare a sample using only a thin film of oil ~100 um or more thick. This can be done by placing a drop of oil onto a substrate and spreading it out using a small tool or spreader. The substrate and sample can then be placed into the measurement system in either a vertical or horizontal orientation, as the surface tension of the liquid and the low viscosity always ensure that the film remains infinitely thick.

The substrate should have the following properties for it to be suitable. It must have an x-ray line around 1 keV, be mechanically rigid, and have a chemical inertness to the oil. Additionally, if it can be cleaned and reused, this is an added bonus. One material which fits these criteria is copper which has L lines at 0.930 keV and 0.950 keV. These lines are efficiently excited by the Mo L line used to excite the sample and can be detected by the detector if the sample is sufficiently thin to allow these x-rays through. However, if the oil film is sufficiently thick as to be "infinitely thick" for Al and Si x-rays, then no Cu L x-rays will be measured.

A clean copper sample can also be used to test that the vacuum is operating correctly in the system, because these x-rays are very rapidly absorbed by air, it can provide an extremely sensitive way of measuring the level of vacuum or purity of Helium in the measurement system. Accordingly, a copper disk can be held by sample holder 26, FIG. 1 after a thin film of oil is spread across the copper disk.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. A fuel analysis system comprising:
   an x-ray source which emits x-rays at an energy level below but proximate the absorption edge of sulfur;
   a monochromator in the optical path between the source and a fuel sample for directing x-rays at a single energy level at the fuel sample to limit excitation of any sulfur in the fuel sample;
   a detector responsive to x-rays emitted by the sample; and
   an analyzer responsive to the detector and configured to detect at least one element in the sample.

2. The analysis system of claim 1 in which the x-ray source is a molybdenum anode x-ray tube.

3. The analysis system of claim 1 in which the monochromator includes doubly curved crystals.

4. The analysis system of claim 1 in which the element include elements chosen from the group consisting of: sodium, magnesium, aluminum, silicon, and phosphorous.

5. A fuel analysis method comprising:
- directing x-rays at a single energy level below but proximate the absorption edge of sulfur at a fuel sample to limit excitation of any sulfur in the fuel sample;
- detecting x-rays emitted by the sample; and
- detecting of at least one catalyst fine in the sample.

6. The method of claim 5 in which the x-ray source is a molybdenum anode x-ray tube.

7. The method of claim 5 in which the monochromator includes doubly curved crystals.

8. The method of claim 5 in which the catalyst fines include elements chosen from the group consisting of sodium, magnesium, aluminum, silicon, and phosphorous.

* * * * *